US012544280B2

(12) United States Patent
Nash

(10) Patent No.: US 12,544,280 B2
(45) Date of Patent: Feb. 10, 2026

(54) REUSABLE CUTTING ARTICLES AND WOUND TAPE ARTICLES AND KITS CONTAINING THE SAME

(71) Applicant: 3M INNOVATIVE PROPERTIES COMPANY, St. Paul, MN (US)

(72) Inventor: James E. Nash, Bloomington, MN (US)

(73) Assignee: 3M Innovative Properties Company, St. Paul, MN (US)

(*) Notice: Subject to any disclaimer, the term of this patent is extended or adjusted under 35 U.S.C. 154(b) by 431 days.

(21) Appl. No.: 18/014,295

(22) PCT Filed: Jul. 1, 2021

(86) PCT No.: PCT/IB2021/055930
§ 371 (c)(1),
(2) Date: Jan. 3, 2023

(87) PCT Pub. No.: WO2022/009040
PCT Pub. Date: Jan. 13, 2022

(65) Prior Publication Data

US 2023/0255838 A1 Aug. 17, 2023

Related U.S. Application Data

(60) Provisional application No. 63/049,717, filed on Jul. 9, 2020.

(51) Int. Cl.
*A61F 15/02* (2006.01)
*A61F 15/00* (2006.01)
*B65H 35/00* (2006.01)

(52) U.S. Cl.
CPC ............ *A61F 15/02* (2013.01); *A61F 15/002* (2013.01); *B65H 35/002* (2013.01); *B65H 35/008* (2013.01); *B65H 2701/37* (2013.01)

(58) Field of Classification Search
CPC ... A61F 15/002; A61F 15/02; B65H 2701/37; B65H 35/008; B65H 35/002; B65H 35/02
USPC ............................. 225/56, 39, 65; 242/588.6
See application file for complete search history.

(56) References Cited

U.S. PATENT DOCUMENTS 3,743,151 A * 7/1973 Malcolm ............ B65H 35/0026 225/53
3,815,801 A * 6/1974 Perrin ................ B65H 35/0026 225/53
3,972,459 A * 8/1976 Cooper .............. B65H 35/0026 225/49
4,401,248 A * 8/1983 Helms ................ B65H 35/0026 242/588.4
4,627,560 A * 12/1986 Samuelson ........ B65H 35/0026 225/25
4,711,384 A * 12/1987 Harris ................ B65H 35/0026 225/82
4,875,609 A * 10/1989 Elder ................... B65D 85/672 225/48

(Continued)

OTHER PUBLICATIONS

International Search Report for PCT Application No. PCT/IB2021/055930, mailed on Oct. 1, 2021, 4 pages.

*Primary Examiner* — Chun Hoi Cheung

(57) ABSTRACT

Cutting article, for example for cutting tape, that is removable from a container, such as a box, of tape. Wound tape articles containing the same. Kits containing the same.

13 Claims, 9 Drawing Sheets

(56) References Cited

U.S. PATENT DOCUMENTS

| | | | | | |
|---|---|---|---|---|---|
| 4,898,312 | A * | 2/1990 | Hwang | B65H 35/0026 225/26 |
| 4,961,525 | A * | 10/1990 | Corbo | B65H 35/0026 225/56 |
| 5,735,400 | A * | 4/1998 | Packard | B65H 37/00 206/408 |
| 5,820,005 | A * | 10/1998 | Perkitny | B65H 35/0026 225/65 |
| 5,878,932 | A * | 3/1999 | Huang | B65H 35/0026 242/588 |
| 6,293,452 | B1 * | 9/2001 | Mandar | B65H 35/0026 225/41 |
| 6,481,607 | B1 * | 11/2002 | Van Cott | B65H 35/0026 225/48 |
| 7,051,972 | B2 * | 5/2006 | Milliorn | B65H 35/0026 206/408 |
| 7,441,581 | B2 * | 10/2008 | Pitzen | B65H 35/0033 156/577 |
| 8,474,504 | B2 * | 7/2013 | Vulpitta | B65H 35/0073 225/56 |
| 9,809,411 | B2 * | 11/2017 | Tiedemann | B65H 35/0026 |
| 9,908,735 | B2 * | 3/2018 | Tiedemann | B65H 35/002 |
| 2008/0116218 | A1 * | 5/2008 | Lacona | B65D 85/04 225/46 |
| 2009/0179061 | A1 * | 7/2009 | Dureiko | B65H 35/0073 225/56 |
| 2019/0209401 | A1 | 7/2019 | Queen et al. | |

* cited by examiner

REUSABLE CUTTING ARTICLES AND WOUND TAPE ARTICLES AND KITS CONTAINING THE SAME

CROSS REFERENCE TO RELATED APPLICATIONS

This application is a national stage filing under 35 U.S.C. 371 of PCT/IB2021/055930, filed Jul. 1, 2021, which claims the benefit of U.S. Application No. 63/049,717, filed Jul. 9, 2020, the disclosure of which is incorporated by reference in its/their entirety herein.

BACKGROUND

Rolled tape packaged in boxes, such as Scotch® Magic™ tape is known. Such rolled tapes can be placed in dispensers. Rolled tapes that sold in single-use disposable dispensers are also known.

DETAILED DESCRIPTION

Figure 1:
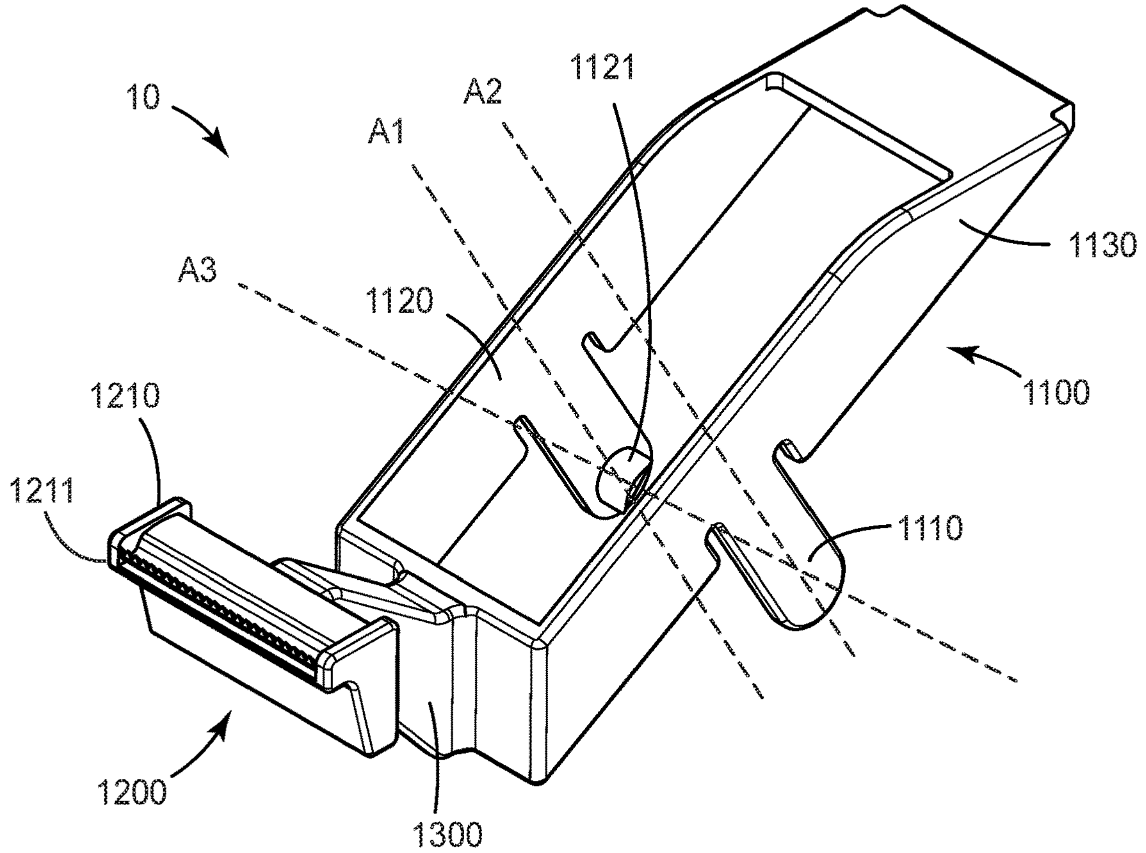
FIG. 1 is three-quarters top-down view of an exemplary removable cutting article.
Figure 2:
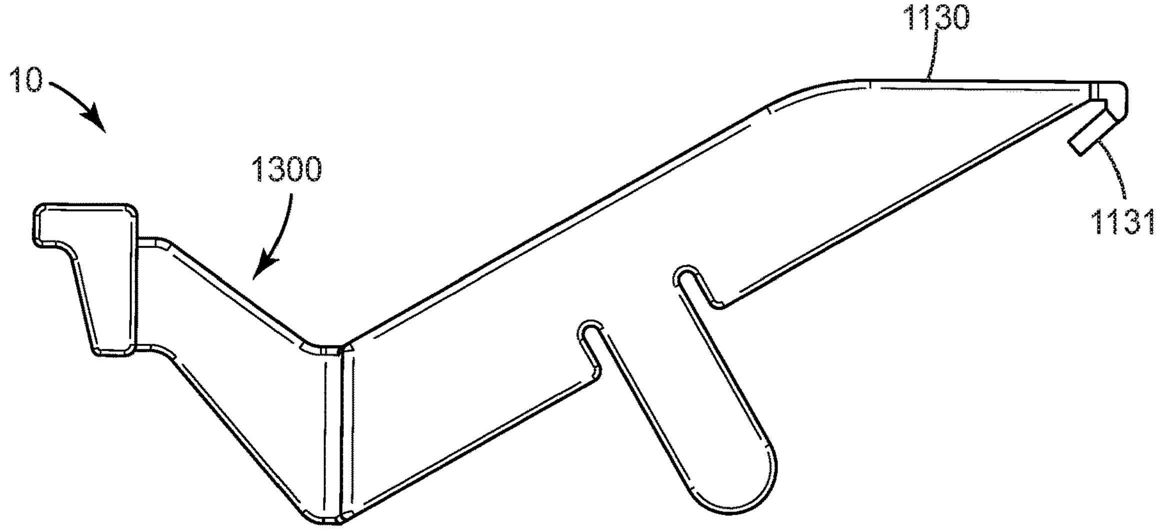
FIG. 2 is a side view of the exemplary removable cutting article as also shown in FIG. 1.
Figure 3:
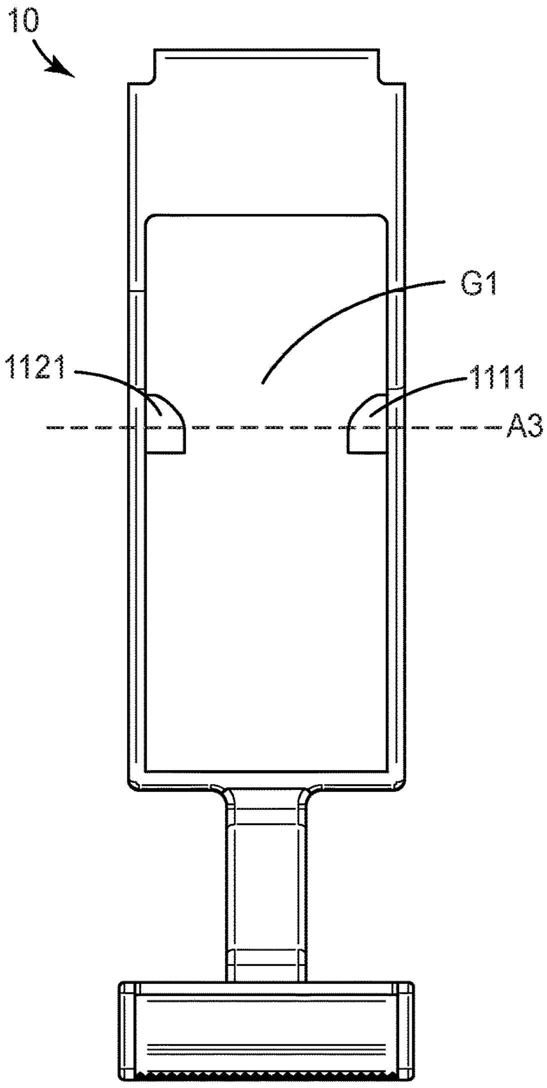
FIG. 3 is a top view of the exemplary removable cutting article as also shown in FIGS. 1-2.
Figure 4:
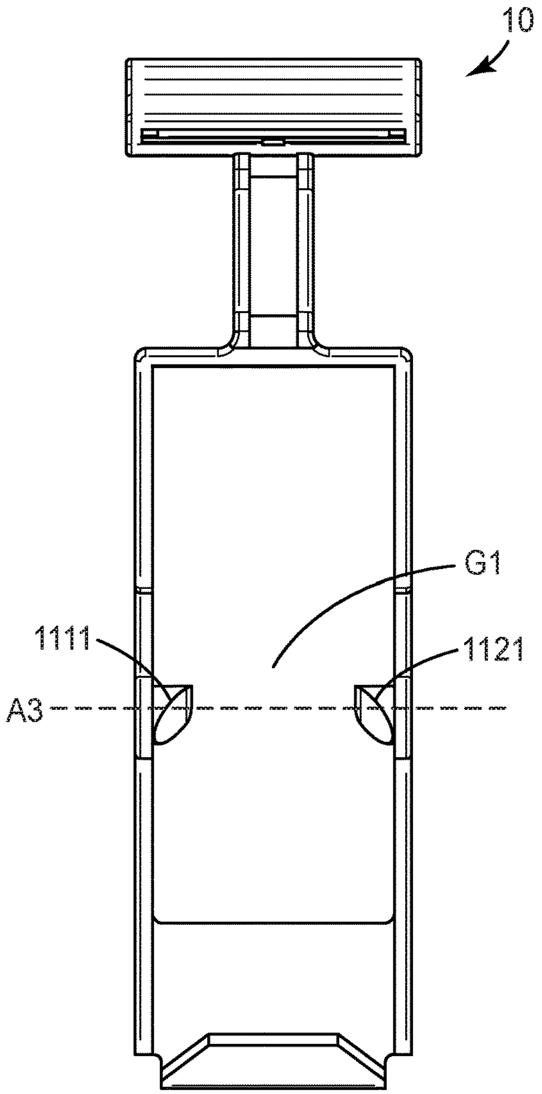
FIG. 4 is a bottom view of the exemplary removable cutting article as also shown in FIGS. 1-3.
Figure 5:
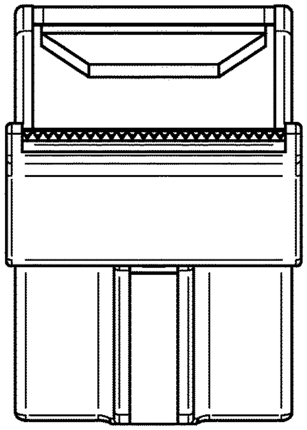
FIG. 5 is a front view of the exemplary removable cutting article as also shown in FIGS. 1-4.
Figure 6:
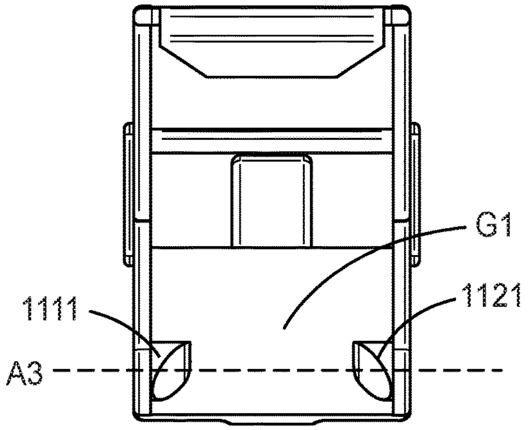
FIG. 6 is a back view of the exemplary removable cutting article as also shown in FIGS. 1-5.
Figure 7:
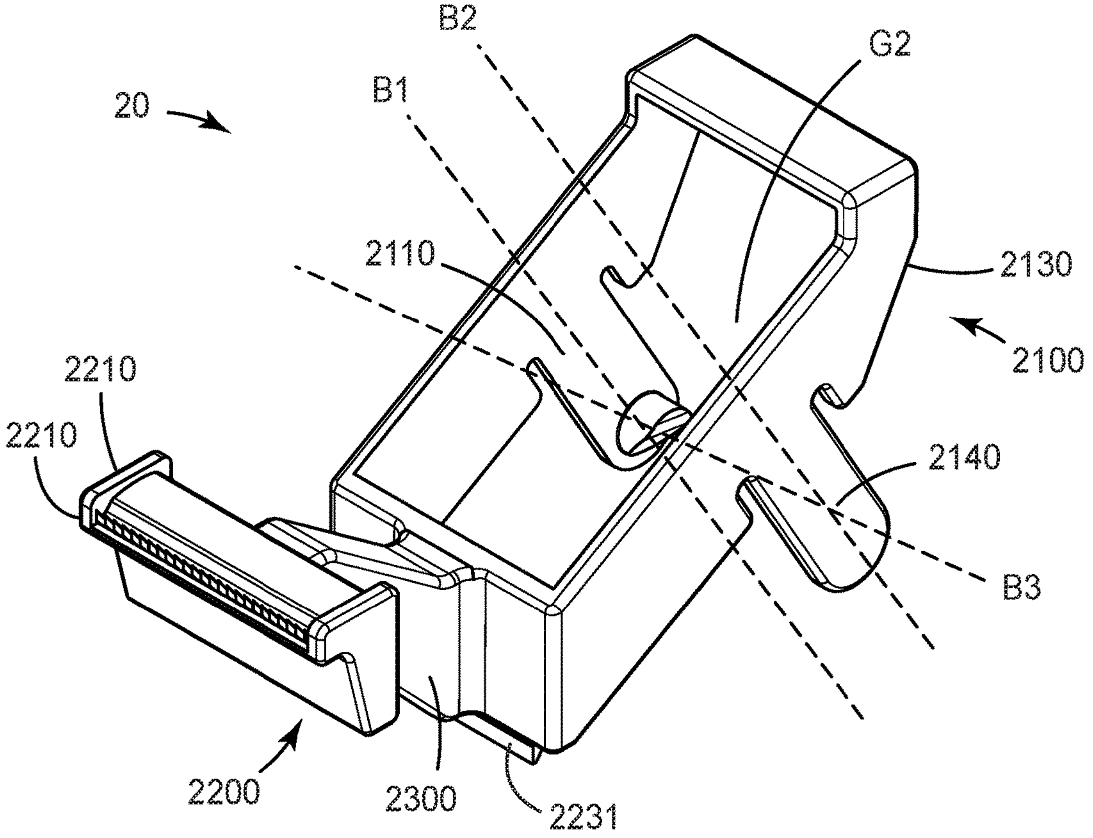
FIG. 7 is a three-quarters top-down view of another exemplary removable cutting article.
Figure 8:
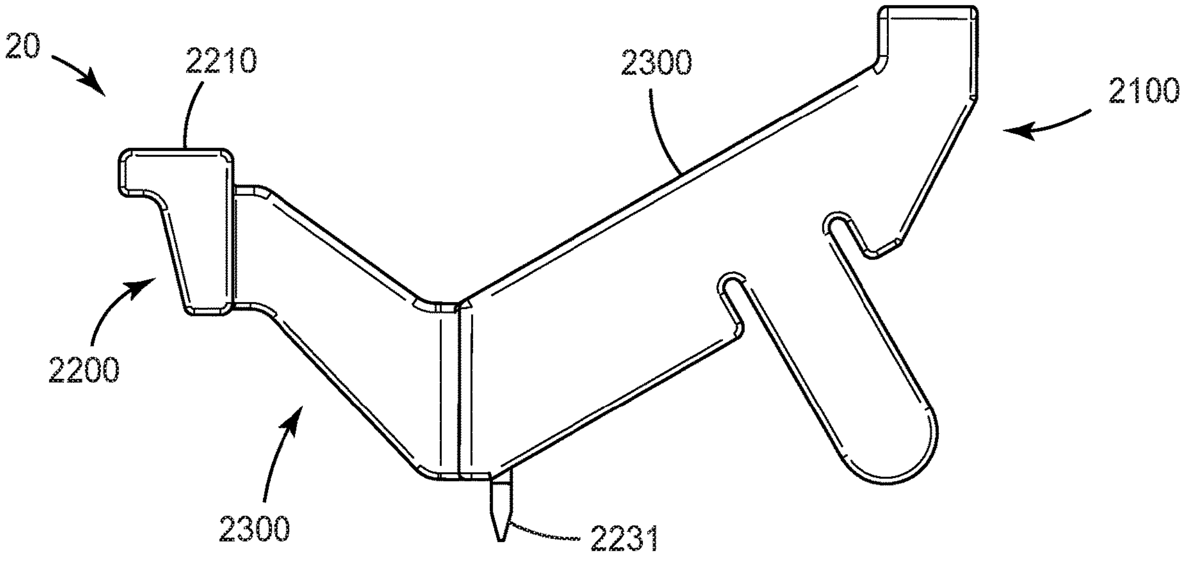
FIG. 8 is aside view of the exemplary removable cutting article as also shown in FIG. 7.
Figure 9:
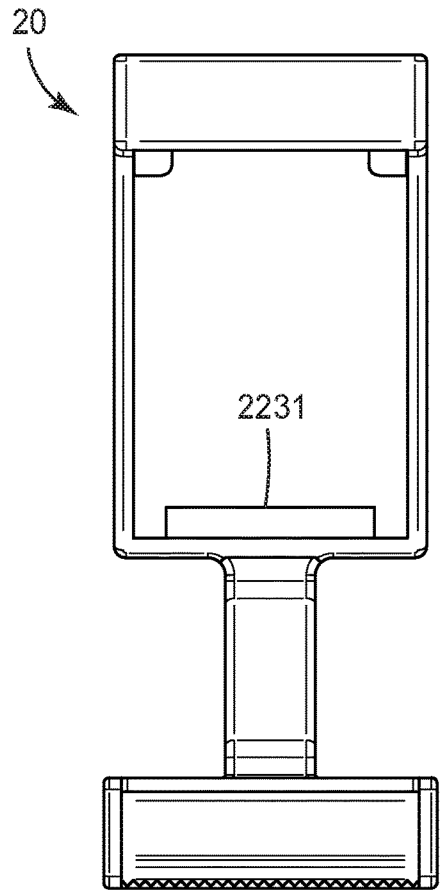
FIG. 9 is a top view of the exemplary removable cutting article as also shown in FIGS. 7-8.
Figure 10:
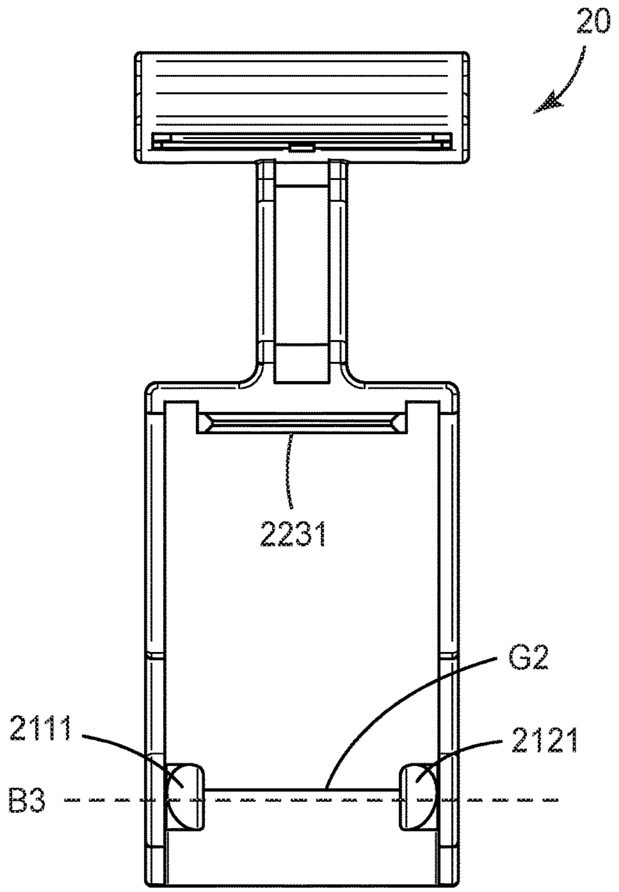
FIG. 10 is a bottom view of the exemplary removable cutting article as also shown in FIGS. 7-9.
Figure 11:
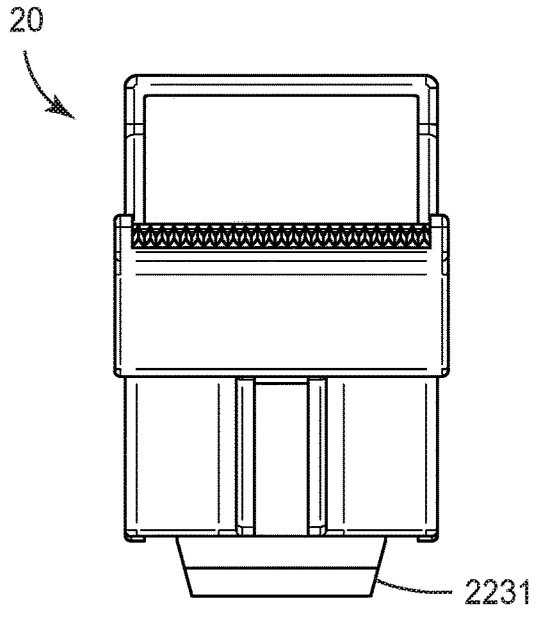
FIG. 11 is a front view of the exemplary removable cutting article as also shown in FIGS. 7-10.
Figure 12:
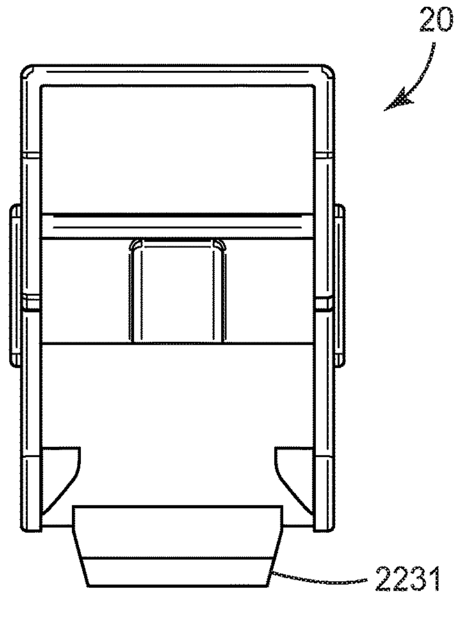
FIG. 12 is a back view of the exemplary removable cutting article as also shown in FIGS. 7-11.
Figure 13:
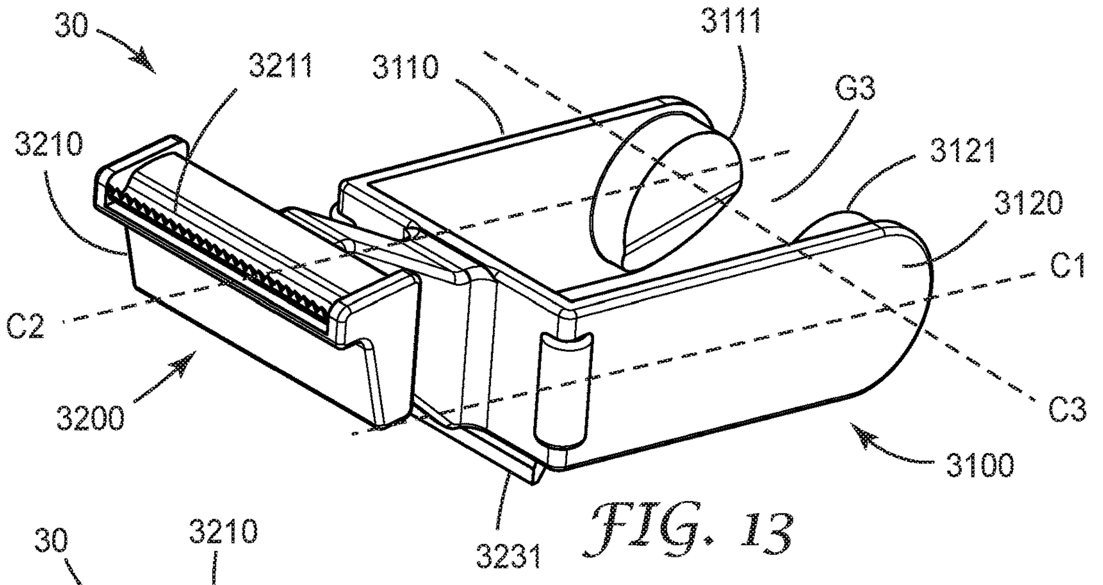
FIG. 13 is a three-quarters top-down view of yet another exemplary removable cutting article.
Figure 14:
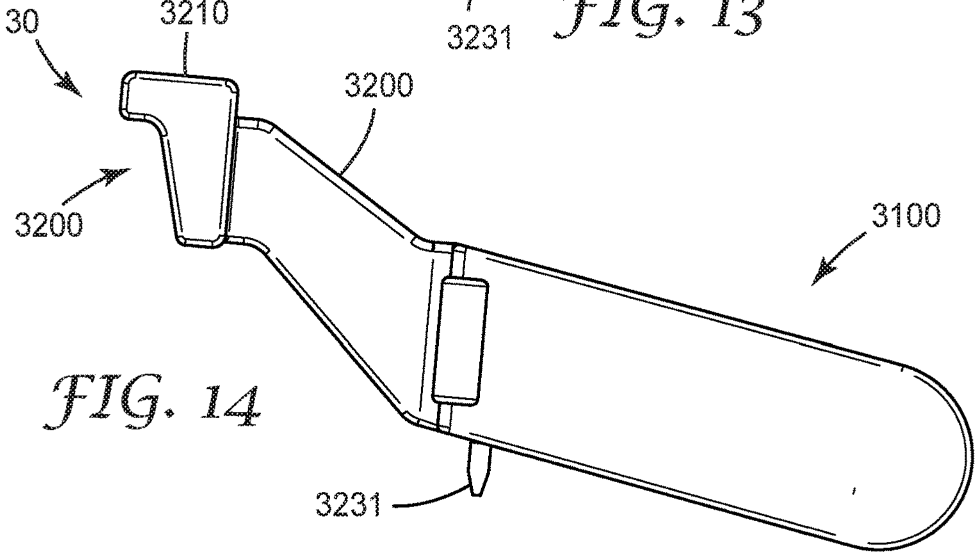
FIG. 14 is a side view of the exemplary removable cutting article as also shown in FIG. 13.
Figure 15:
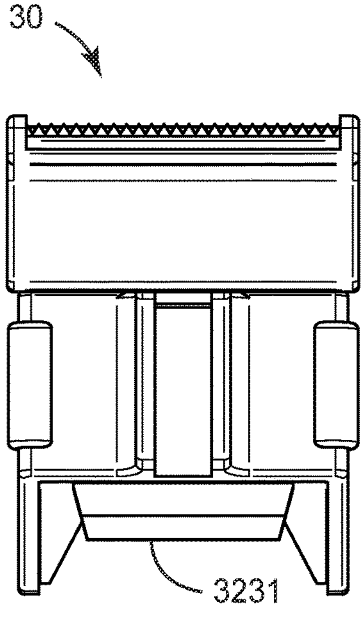
FIG. 15 is a top view of the exemplary removable cutting article as also shown in FIGS. 13-14.
Figure 16:
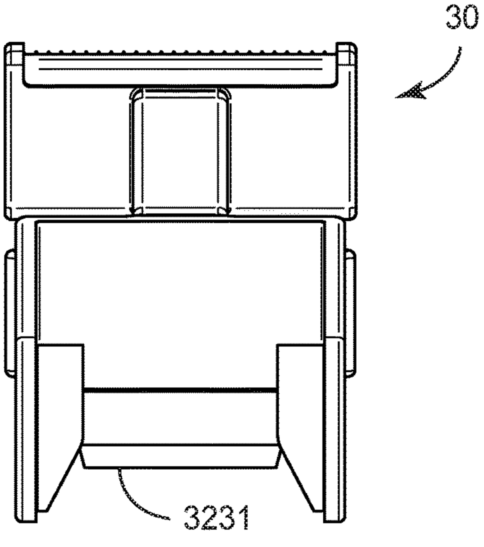
FIG. 16 is a bottom view of the exemplary removable cutting article as also shown in FIGS. 31-15.
Figure 17:
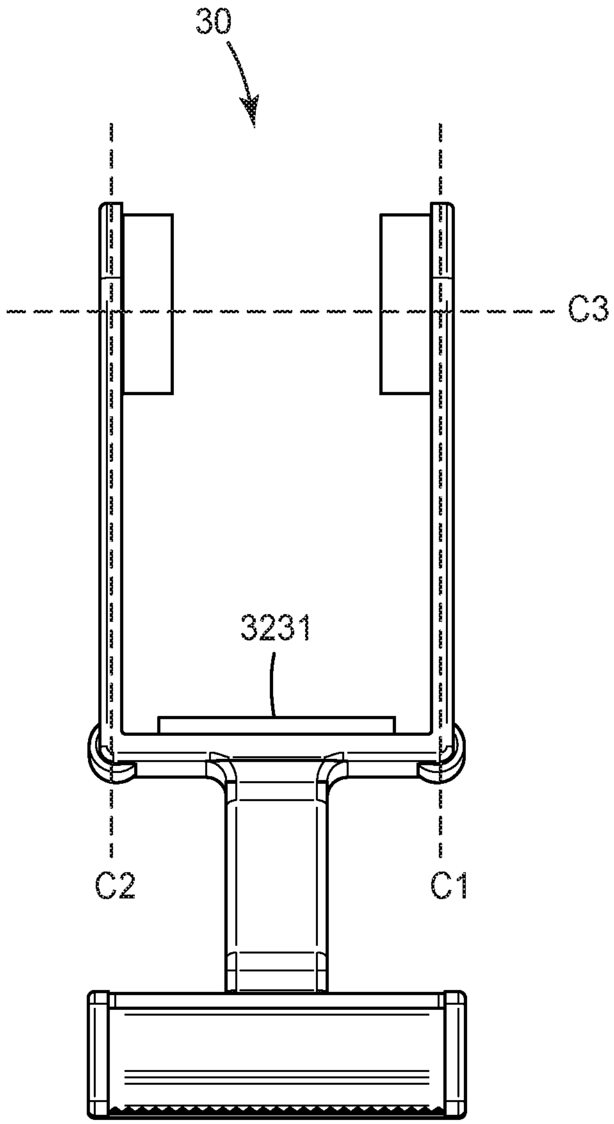
FIG. 17 is a front view of the exemplary removable cutting article as also shown in FIGS. 13-16.
Figure 18:
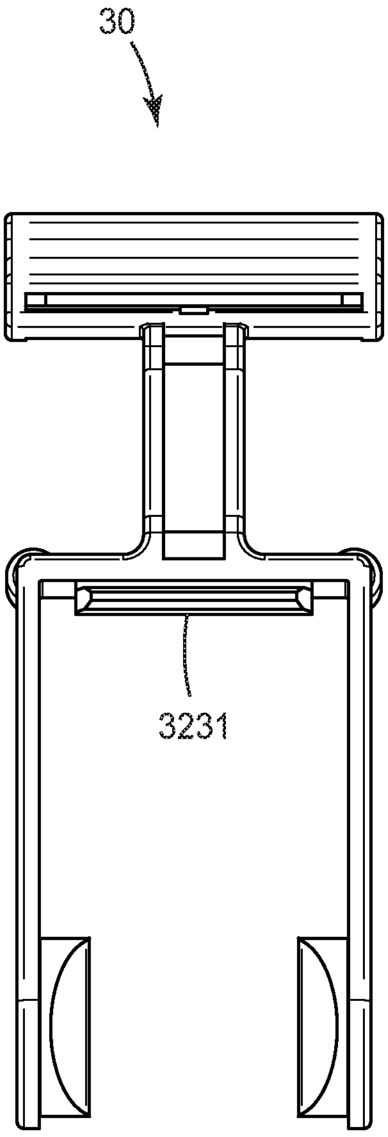
FIG. 18 is a back view of the exemplary removable cutting article as also shown in FIGS. 31-17.

Throughout this disclosure, singular forms such as "a," "an," and "the" are often used for convenience; however, the singular forms are meant to include the plural unless the singular alone is explicitly specified or is clearly indicated by the context. When the singular alone is called for, the term "one and only one" is typically used.

Some terms in this disclosure are defined below. Other terms will be familiar to the person of skill in the art and should be afforded the meaning that a person of ordinary skill in the art would have ascribed to them.

Terms indicating a high frequency, such as (but not limited to) "common," "typical," and "usual," as well as "commonly," "typically," and "usually" are used herein to refer to features that are often employed in the invention and, unless specifically used with reference to the prior art, are not intended to mean that the features are present in the prior art, much less that those features are common, usual, or typical in the prior art.

Current wound tape products are often sold in disposable dispensers that are designed to be disposed of after a single roll of tape is consumed. These are very convenient because there is no need to load the tape roll into a dispenser, but they generate a large amount of waste. Typically, the disposable dispenser is plastic. Even if it were possible to recycle the plastic dispenser, the use of plastic can be environmentally problematic as it has been reported that only 9% of plastic in the United States is recycled. Compostable plastic dispensers are not known.

Other current wound tape products are sold in boxes to be placed in reusable dispensers. The boxes are often made of recyclable or compostable paper or cardboard, however they are less convenient to use than wound tape products that are sold in a disposable dispenser because they need to be loaded into a reusable dispenser before they can be conveniently used.

This disclosure provides a solution to the foregoing problems and other problems. Briefly, reusable cutting articles, as well as wound tape articles and kits containing the reusable cutting article, that addresse the disadvantages of both formerly known wound tape products. A removable cutting article is configured to releasably engage with a box, such as a box containing a wound tape article, that has a box top, a box front and opposing box back, and two opposite box sides.

FIGS. 1-6 show removable cutting article 10 comprising distal end 1100 and proximal end 1200 spaced apart by spacing member 1300. Distal end 1100 includes two arms 1110, 1120 extending along a first axis A1 and parallel second axis A2, each of which has a protrusion 1111, 1121 extending into gap G1 that separates arms 1100, 1200 along third axis A3. Third axis A3 is substantially orthogonal to first axis A1 and second axis A2. Distal end 1100 also includes housing 1130, which in turn comprises clip 1131. Proximal end 1200 includes cutting element 1210 which is spaced from the two arms 1100, 1200 by spacing member 1300 and comprises sharp edge 1211.

FIGS. 7-12 show removable cutting article 20 comprising a distal end 2100 and proximal end 2200 spaced apart by spacing member 2300. Distal end 2100 includes two arms 2110, 2120. Distal end 2100 includes two arms 2110, 2120 extending along a first axis B1 and parallel second axis B2, each of which has a protrusion 2111, 2121 extending into gap G2 that separates arms 2100, 2200 along third axis B3. Third axis B3 is substantially orthogonal to first axis B1 and second axis B2. Distal end 2100 also comprises housing 2130. Proximal end 2200 includes cutting element 2210 which is spaced from the two arms 2100, 2200 by spacing member 2300 and comprises sharp edge 2211. Clip 2231 is also present on proximal end 2200

FIGS. 13-18 show removable cutting article 30 comprising a distal end 3100 and proximal end 3200 spaced apart by spacing member 3300. Distal end 3100 includes two arms 3110, 3120 extending along a first axis C1 and parallel second axis C2, each of which has a protrusion 3111, 3121 extending into gap G3 that separates arms 3100, 3200 along third axis C3. Third axis C3 is substantially orthogonal to first axis B1 and second axis B2. Removable cutting article 30 does not have a housing component to distal end 3100. Proximal end 3200 includes cutting element 3210 which is spaced from the two arms 3100, 3200 by spacing member 3300 and comprises sharp edge 3211. Clip 3231 is also present on proximal end 3200

A wound tape article can be formed by placing a removable cutting article on a box that contains tape. Any removable cutting article disclosed herein can be used for this purpose. The box containing the tape can have one or more openings for attaching the removable cutting article. The one or more openings can be made in any suitable way or shape. For example, openings pre-formed in the box, or there can be perforations or scores in where the openings are to be formed by a user when the removable cutting article is placed on the box.

Figure 19:
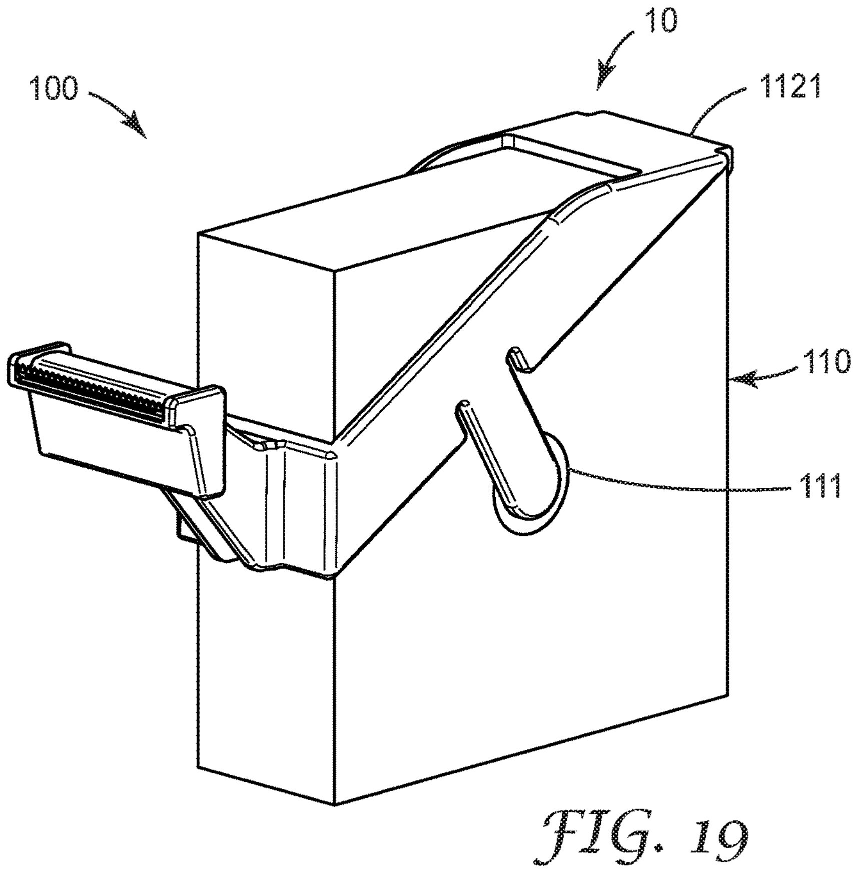
FIG. 19 is a view of the removable cutting article of FIGS. 1-6 affixed to a box.

FIG. 19 shows removable cutting article 10, which is depicted in more detail in FIGS. 1-6, as a component of wound tape article 100, that also includes box 110 having opening 111 for receiving protrusions 1111, 1121 (not visible in this Figure). Clip 1131 helps secure removable cutting article 10 on box 110, either by gripping the outside of box 110 or by punching out a perforation (not shown) in an appropriate location on box 110. Not visible in this Figure is a wound tape roll within box 110.

Figure 20:
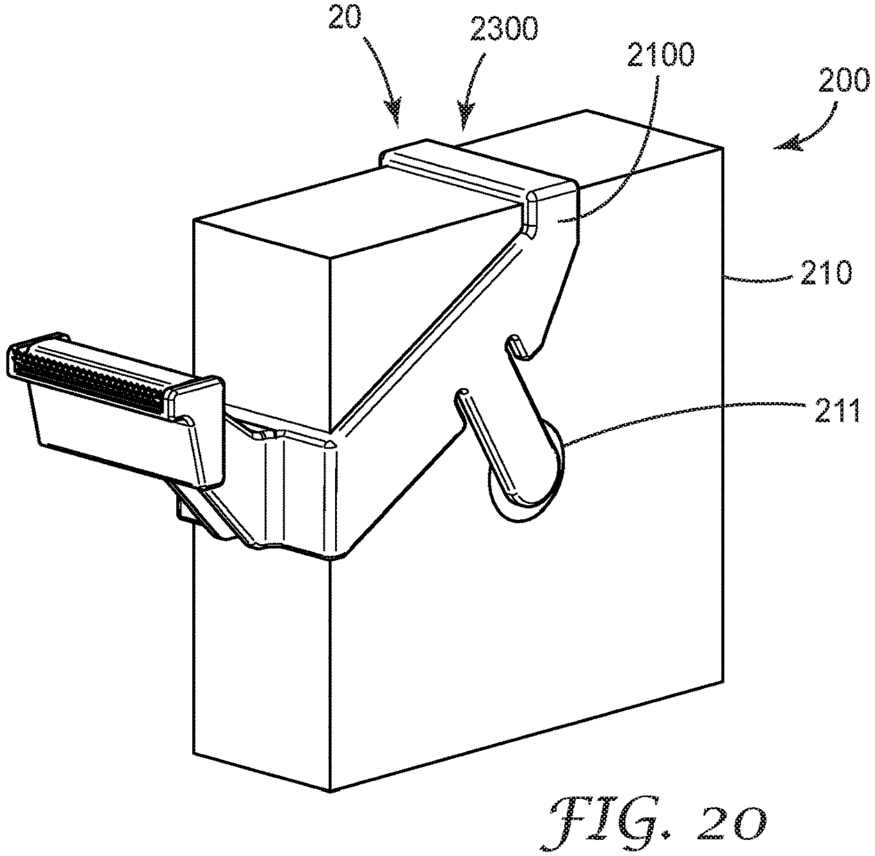
FIG. 20 is a view of the removable cutting article of FIGS. 7-12 affixed to a box.

FIG. 20 shows removable cutting article 20, which is depicted in more detail in FIGS. 7-12, as a component of wound tape article 200, that also includes box 210 having opening 211 for receiving protrusions 2111, 2121 (not visible in this Figure). Housing 2300 of distal end 2100 is configured to help retain removable cutting element 20 on box 210. Clip 2231 (not visible in this figure) helps secure removable cutting article 20 to box 210 by punching out a perforation (not shown) in an appropriate location on box 210.

Figure 21:
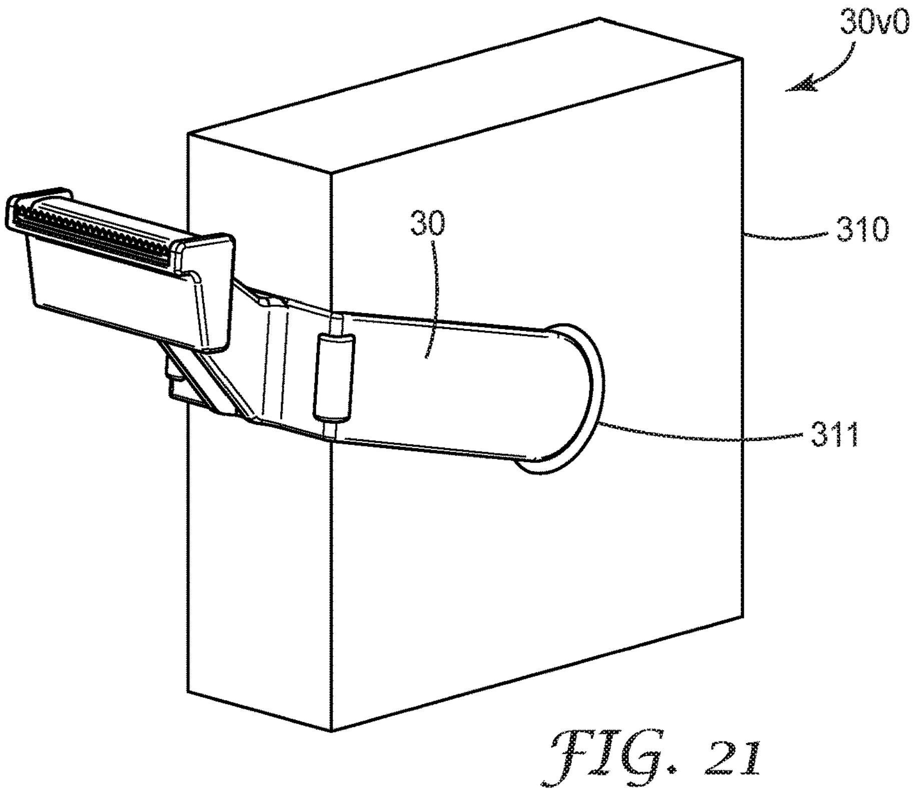
FIG. 21 is a view of the removable cutting article of FIGS. 13-18 affixed to a box.

FIG. 21 shows removable cutting article 30, which is depicted in more detail in FIGS. 13-18, as a component of wound tape article 300, that also includes box 310 and opening 311 for receiving protrusions 3111, 3121 (not visible in this Figure). Proximal end 3200 of removable cutting article 30 is configured to keep removable cutting article 30 in place on box 310. Clip 3231 (not visible in this figure) helps secure removable cutting article 30 to box 310 by punching out a perforation (not shown) in an appropriate location on box 310. Alternatively, clip 3231 might be inserted into a pre-existing slot (rather than using perforations).

Figure 22:
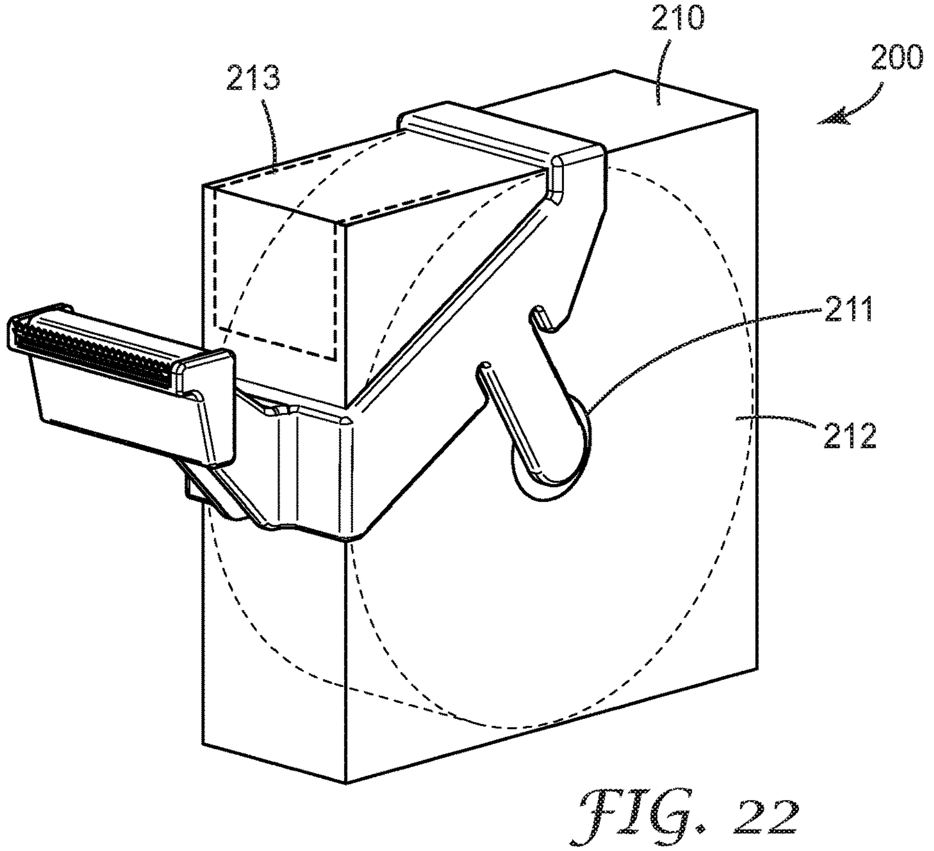
FIG. 22 is a view of a wound tape article featuring the removable cutting article of FIGS. 7-12.
Figure 23:
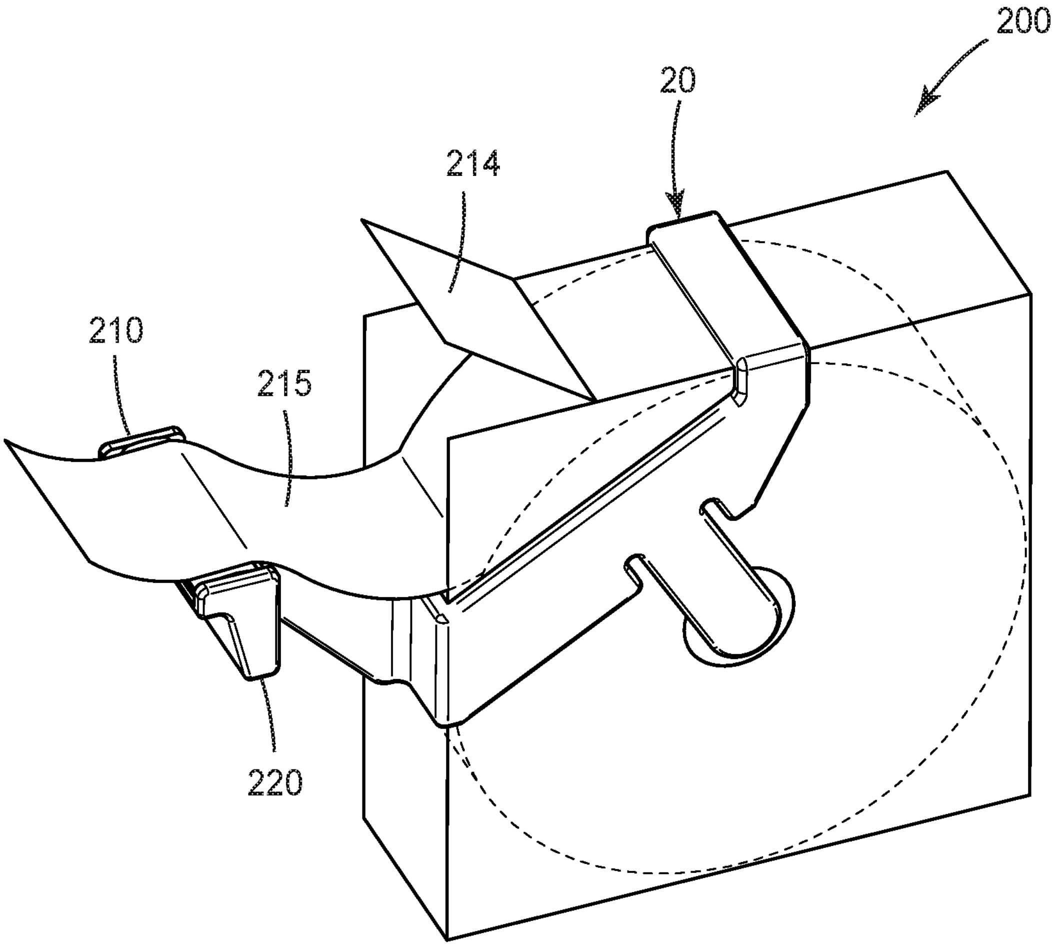
FIG. 23 is a view of a wound tape article featuring the removable cutting article of FIGS. 7-12.

As an example of how the removable cutting articles and wound tape articles herein may be used, FIGS. 22 and 23 depict wound tape article 200 having tape roll 212 located such that the center of tape roll 212 is aligned with opening 211. A core (not visible in this Figure) may optionally be employed to retain tape roll 212 centered on protrusions 3111, 3121 (not visible in this Figure) as tape is removed from tape roll 212. Perforations 213 (FIG. 22) allow access to tape roll 212.

When perforations 213 are torn, flap 214 allows access to tape 215, which can be unrolled to the desired length over proximal end 2200, and more specifically cutting element 2210, of removable cutting article 20. This allows the wound tape article 200 to be used in essentially the same manner as a standard tape dispenser.

Any type of tape that can be wound can be employed, including tapes with single-sided or double-sided adhesive, foam tapes, cellulose based tapes, masking tapes, conspicuity tapes, magnetic tape, and the like. The tapes may have, for example, a circular core or a flat core (flat-wound tape), or they may have no core. One exemplary tape that can be used is the tape available as SCOTCH® Brand MAGIC™ TAPE (3M Company, St. Paul, MN, USA); other types of tape can also be employed.

A removable cutting article, such as those described herein, can be included as part of a kit with one or more, such as one to 6, rolls or boxes of tape. The removable cutting article can be attached to a roll or box of tape as shown in the Figures to make wound tape articles.

What is claimed is:

1. A wound tape article comprising a box containing a wound tape roll and a removable cutting article removably attached to the box, wherein the removable cutting article for releasably engaging with the box has a box top, a box front and opposing box back, and two opposite box sides, the removable cutting article comprising:

a distal end and a proximal end connected by a spacing member;

the distal end comprising two arms that are spaced apart from each other and that are oriented along a first axis and a second axis parallel to the first axis, wherein each of the two arms having a protrusion that extends from the arms and towards each other along a third axis that is orthogonal to the first axis;

the proximal end comprising at least one cutting element spaced from the at least two arms, the cutting element having a sharp edge that is disposed along a fourth axis that is parallel to the third axis.

2. The removable cutting article of claim 1, wherein the two arms are separated by a gap and further wherein the protrusion of each of the two arms extends into the gap.

3. The removable cutting article of claim 1, wherein distal end further comprises a housing that is connected to the two arms.

4. The removable cutting article of claim 1, wherein the housing comprises space for engaging with the box.

5. The removable cutting article of claim 1, wherein the housing comprises a back for engaging with the box top.

6. The removable cutting article of claim 1, wherein the housing comprises a back for engaging with the box back.

7. The wound tape article of claim 1, wherein the box sides each comprise a hole for receiving the at least a portion of the protrusions of the removing cutting article, and wherein at least a portion of one of the protrusions are disposed within each hole.

8. The wound tape article of claim 7, wherein the holes are aligned with a core within the box, wherein the tape is wound around the core.

9. The wound tape article of claim 1, wherein the box comprises an opening in the box front or the box top for removing the tape and wherein the sharp edge is spaced from the box front and is located between the opening and the box bottom.

10. The wound tape article of claim 1, further comprising a core around which the tape is wound, the core comprising a hollow center, within the box, and wherein the tape is wound around the core.

11. The wound tape article of claim 1, wherein the box comprises perforations.

12. A kit comprising a plurality of boxes that one wound roll of tape; and a removable cutting article of claim 1.

13. The kit of claim 12, comprising from one to twenty, from one to ten, and optionally from one to six boxes that contain one wound roll of tape.

* * * * *